United States Patent [19]
Mayer

[11] Patent Number: 5,390,539
[45] Date of Patent: Feb. 21, 1995

[54] DEVICE FOR MEASURING THE PERMEABILITY OF A MEMBRANE TO WATER VAPOR

[75] Inventor: Daniel W. Mayer, St. Paul, Minn.

[73] Assignee: Modern Controls, Inc., Minneapolis, Minn.

[21] Appl. No.: 126,921

[22] Filed: Sep. 27, 1993

Related U.S. Application Data

[63] Continuation-in-part of Ser. No. 951,235, Sep. 25, 1992, abandoned.

[51] Int. Cl.6 .................. G01N 15/08; G01N 21/17
[52] U.S. Cl. .................................. 73/38; 250/343
[58] Field of Search ............ 73/38, 29.01; 250/343

[56] References Cited

U.S. PATENT DOCUMENTS

| | | | |
|---|---|---|---|
| 2,878,388 | 3/1959 | Bergson | 250/343 |
| 3,498,110 | 3/1970 | Brun | 73/38 |
| 3,604,246 | 9/1971 | Toren | 73/38 |
| 3,618,361 | 11/1971 | Stephens et al. | 73/38 |
| 3,901,820 | 8/1975 | Wood | 250/343 |
| 4,464,927 | 8/1984 | Reid | 73/38 |

Primary Examiner—Hezron E. Williams
Assistant Examiner—Michael J. Brock
Attorney, Agent, or Firm—Palmatier, Sjoquist & Helget

[57] ABSTRACT

A system for measuring the permeability of membranes, particularly with reference to water vapor, utilizing a diffusion cell having a first water vapor chamber and a second gas flow chamber, the chambers being separated by the membrane to be tested. Gas flow through the gas flow chamber is conveyed to an infrared gas analyzer and to a gas flow sensor; the infrared analyzer provides an electrical signal representative of the water vapor content of the gas, and the gas flow sensor provides a signal representative of the rate of gas flow through the system; the analyzer signal is conveyed to an amplifier and the gas flow sensor signal is utilized to adjust the gain of the amplifier, the output of the amplifier thereby presenting a water vapor signal which has been adjusted to compensate for air flow through the system.

7 Claims, 4 Drawing Sheets

DEVICE FOR MEASURING THE PERMEABILITY OF A MEMBRANE TO WATER VAPOR

This is a continuation-in-part of U.S. application Ser. No. 07/951,235, filed Sep. 25, 1992, and now abandoned.

BACKGROUND OF THE INVENTION

The present invention relates generally to devices for measuring the rate of transmission of a gas or vapor through permeable packaging materials. More particularly, the invention relates to an apparatus for measuring water vapor concentrations in a gaseous medium under various flow conditions.

U.S. Pat. No. 3,902,068, issued Aug. 26, 1975, discloses a Method and Apparatus for Measuring Gas Transmission Through Packaging Materials, wherein an infrared analyzer is used in conjunction with a pumping system, wherein the pumping system cyclically increases and decreases the gas density within an absorption cell of the infrared gas analyzer. The present invention relates to the aforesaid patent, wherein it is contemplated to use a similar type infrared gas analyzer with pressure pulsations within the absorption cell. However, the aforesaid patent was concerned with measuring the permeation of various gases and vapors through packaging material by accumulation of gases, whereas the present invention relates to measuring water vapor transmission through packaging materials under dynamic flow conditions of a carrier gas.

SUMMARY OF THE INVENTION

A permeation cell is utilized, wherein a sample of packaging material may be clamped between two cell chambers, and one of the chambers may be filled or partially filed with water. A carrier gas is passed through the other chamber, and thereafter into an absorption cell of an infrared gas analyzer. The gas is conveyed away from the absorption cell through a gas flow meter, wherein the volume flow rate of the gas is measured. The water vapor absorbed in the carrier gas is thereby conveyed serially to the absorption cell and through the flow meter, and the absorption cell utilizes an infrared sensor to measure the water vapor concentration in the absorption cell, and to generate an electrical signal representative of this concentration. The flow measuring device measures the flow rate of the gas, generating an electrical signal representative thereof, and the two electrical signals are passed through an adjustable gain amplifier to drive a recording device or display device. The gas flow rate signal is utilized to adjust the gain of the amplifier so as to compensate for variable flow rate conditions, and the adjusted gain output signal generates a signal for displaying the relative water vapor concentration in the carrier gas.

It is the principal object of the present invention to provide an apparatus for measuring the permeability of a packaging material to water vapor transmission.

It is another object of the present invention to provide an apparatus for measuring water vapor concentration in a flowing gas.

It is yet another object of the present invention to provide an apparatus for measuring water vapor concentration through the use of an infrared gas analyzer, and to modify the measured water vapor concentration to compensate for gas flow variations through the system.

BRIEF DESCRIPTION OF THE DRAWINGS

The foregoing and other objects and advantages will become apparent from the following specification and claims, and with reference to the drawings, in which:

DESCRIPTION OF THE PREFERRED EMBODIMENT

Figure 1A:
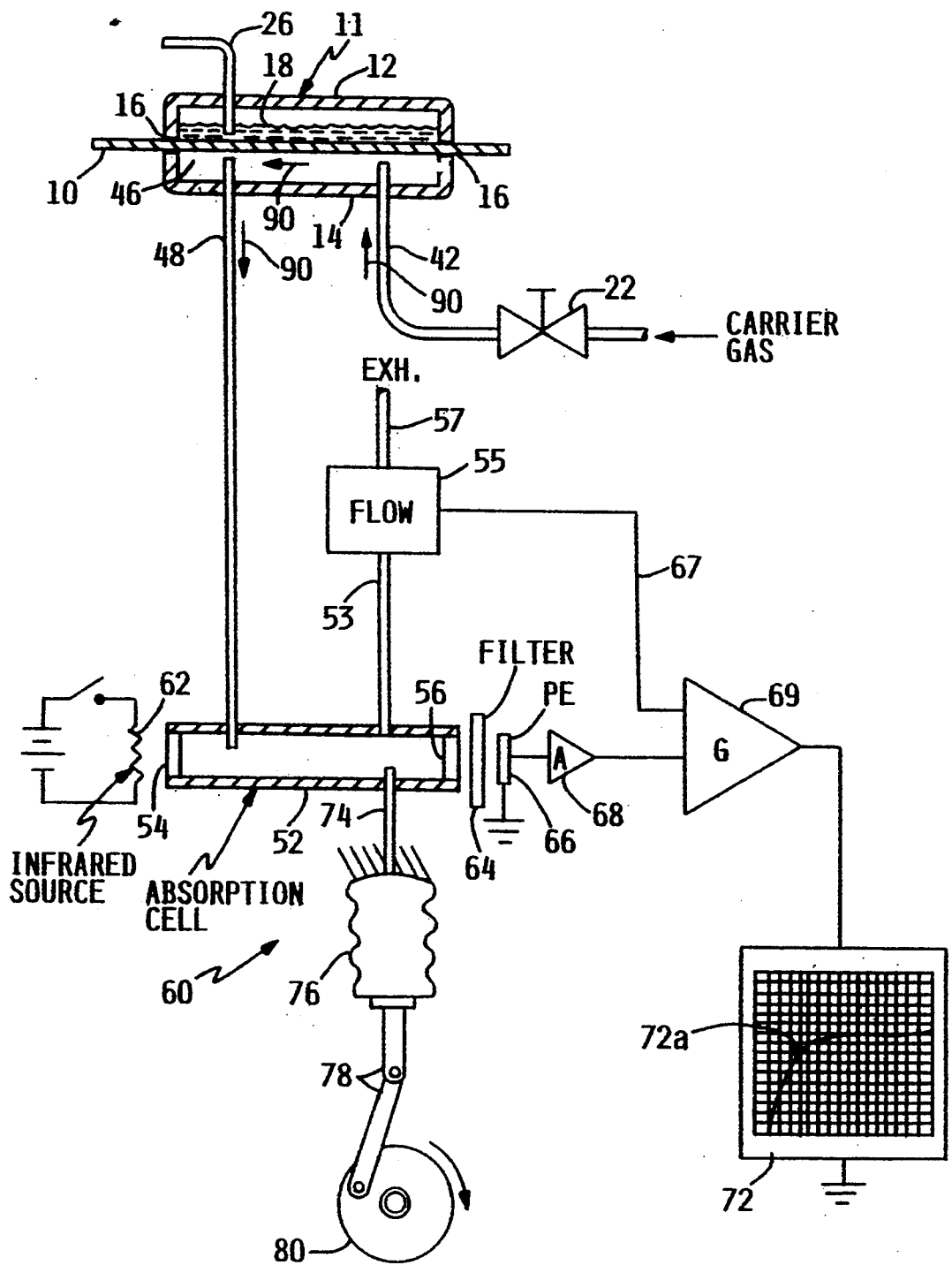
FIG. 1A is a diagrammatic representation of an apparatus showing a preferred form of the invention.

The present invention relates to the invention disclosed in U.S. Pat. No. 3,902,068, which is incorporated herein by reference. Referring first to FIG. 1A, there is shown a diffusion cell 11 comprising two separable halves, including an upper casing 12 and a lower casing 14. The upper and lower casings are shown in cross section in FIG. 1A, and the packaging material to be tested is shown as a film 10 which is clamped between the upper and lower chambers to provide a gas-sealed separation between the two chambers.

The following description of the preferred embodiment is made with reference to the detection of water vapor and the measurement of membrane permeability to water vapor. However, the principles described herein are equally applicable to the detection and measurement of a wide variety of other gases; for example, methane, carbon dioxide and other gases. In such cases, the gas to be measured would be placed into the chamber described herein for holding the water or humid gas.

The upper casing 12 forms a cavity or chamber 18 into which a volume of water is introduced, using a damp sponge or via a tube 26. Upper chamber 18 has a sufficient quantity of water so as to provide a completely saturated chamber, one wall of which is formed by the film 10.

A dry carrier gas such as nitrogen, helium or argon, or other type of inert gas, is conveyed under pressure into the lower chamber 46 of diffusion cell 11, via an adjustable metering valve 22 and tube 42. The gas flow direction is shown by the arrows 90. The carrier gas leaves chamber 46 via tube 48. Tube 48 is connected to absorption cell 52. The absorption cell 52 is connected via tube 53 to a flow meter 55. The output of flow meter 55 is coupled via a tube 57 to an exhaust port. One form of flow meter 53 which is particularly useful in connection with the present invention is a "Microbridge Mass Airflow Sensor," manufactured by the Micro Switch Division of Honeywell. This airflow sensor provides actual mass flow sensing capabilities, and is sensitive to flows in the rate of 0–200 standard cubic centimeters per minute (sccm). It provides an analog output signal representative of the sensed flow rate. The airflow sensor operates on the theory of heat transfer due to mass airflow directed across the surface of a sensing element. The output voltage varies in proportion to the mass air or other gas flow through the inlet and outlet ports of the sensor. It is identified by the manufacturer as a microbridge AWM2000 series, developing an output voltage varying from 0–45 millivolts (mV), as the measured airflow varies from 0–200 sccm.

Cell 52 forms a part of infrared gas analyzer 60, which also includes a source of infrared energy 62 positioned adjacent window 54. The IR source 62 provides radiant energy that passes completely through the cell 52 and windows 54 and 56, and then through an interference filter 64 which is selected so as to transmit a narrow band of radiation centered near 2.6 microns, which is one of the wavelengths at which water vapor provides high attenuation of IR energy. The infrared source 62 may generate radiation broadly over the infrared spectrum from 0.76-200 microns, and the presence of water vapor will attenuate this radiation at certain narrow band segments of the overall wavelength. One of these attenuation segments lies at about 2.6 microns, which is why the interference filter 64 is selected to transmit radiation at this wavelength. Of course, other attenuation bands exist for water vapor within the IR spectrum, and other interference filters associated with these attenuation bands would also be suitably usable with the invention.

After passing through the filter 64 the radiation impinges upon a photoelectric cell 66. Photocell 66 converts the impinging radiation into an electrical signal which is conveyed to an amplifier 68, where the electrical signal is suitably amplified. The output from amplifier 68 is conveyed to a variable gain amplifier "G," designated as 69, and the output from variable gain amplifier 69 is conveyed to a display device, such as strip chart recorder 72. The gain of variable gain amplifier 69 is adjusted by a signal via line 67, which originates in flow sensor 55. This signal is directly proportional to the volume flow rate of gas passing through flow sensor 55. The gain of amplifier 69 is inversely proportional to the signal conveyed via line 67; therefore, as the flow rate increases through flow sensor 55 the gain of the output signal from IR gas analyzer 60 is correspondingly reduced.

Figure 1B:
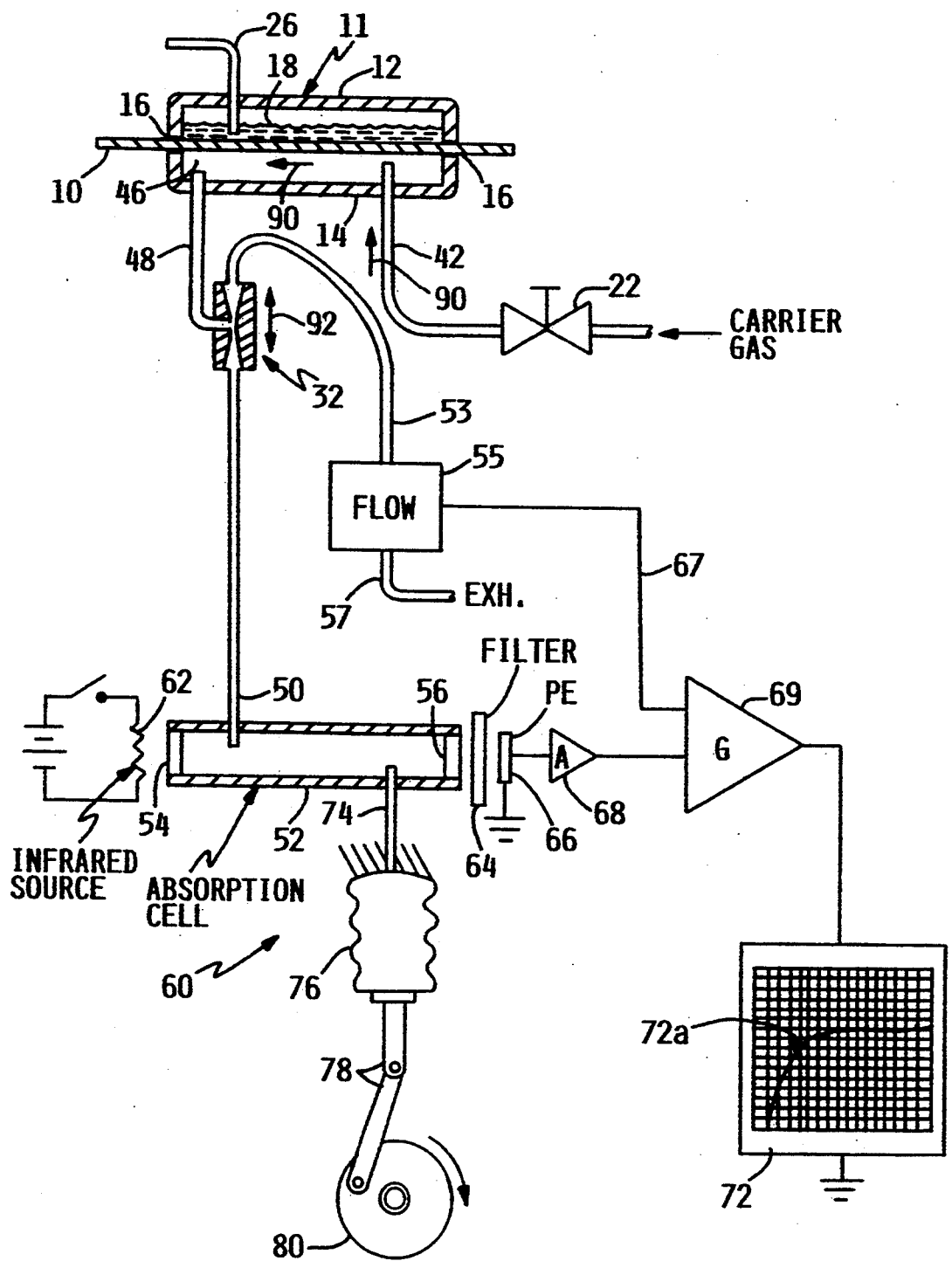
FIG. 1B is a diagrammatic representation of an alternative form of the invention.

FIG. 1B shows an alternative embodiment of the invention, wherein like numerals correspond to the same elements as illustrated in FIG. 1A. The embodiment of FIG. 1B is preferably utilized in situations where the carrier gas is delivered under ambient pressure conditions; one example of such a carrier gas would be ambient air. In this embodiment, tube 48 extends from the diffusion cell chamber 14 to the center point of a venturi 32. One end of the venturi is connected via tube 50 to absorption cell 52, and the other end of the venturi is connected via tube 53 to flow meter 55. Venturi 32 is described in the aforementioned U.S. Pat. No. 3,902,068, which is incorporated by reference herein.

Since the gas flow through venturi 32 is determined by the action of bellows 76, the gas flow will tend to be oscillatory as is indicated by arrow 92. The center tap of venturi 32 is inherently at reduced pressure, thereby creating a net flow of the carrier gas and water vapor mixture within chamber 76 in the direction shown by arrows 90. This carrier gas and water vapor mixture will be drawn into the venturi center tap, and will diffuse throughout the tubes connected thereto, and into the absorption cell 52. In all other respects, the operation of the embodiments of the invention shown in FIGS. 1A and 1B are essentially the same, and will be described hereinafter.

Figure 2:
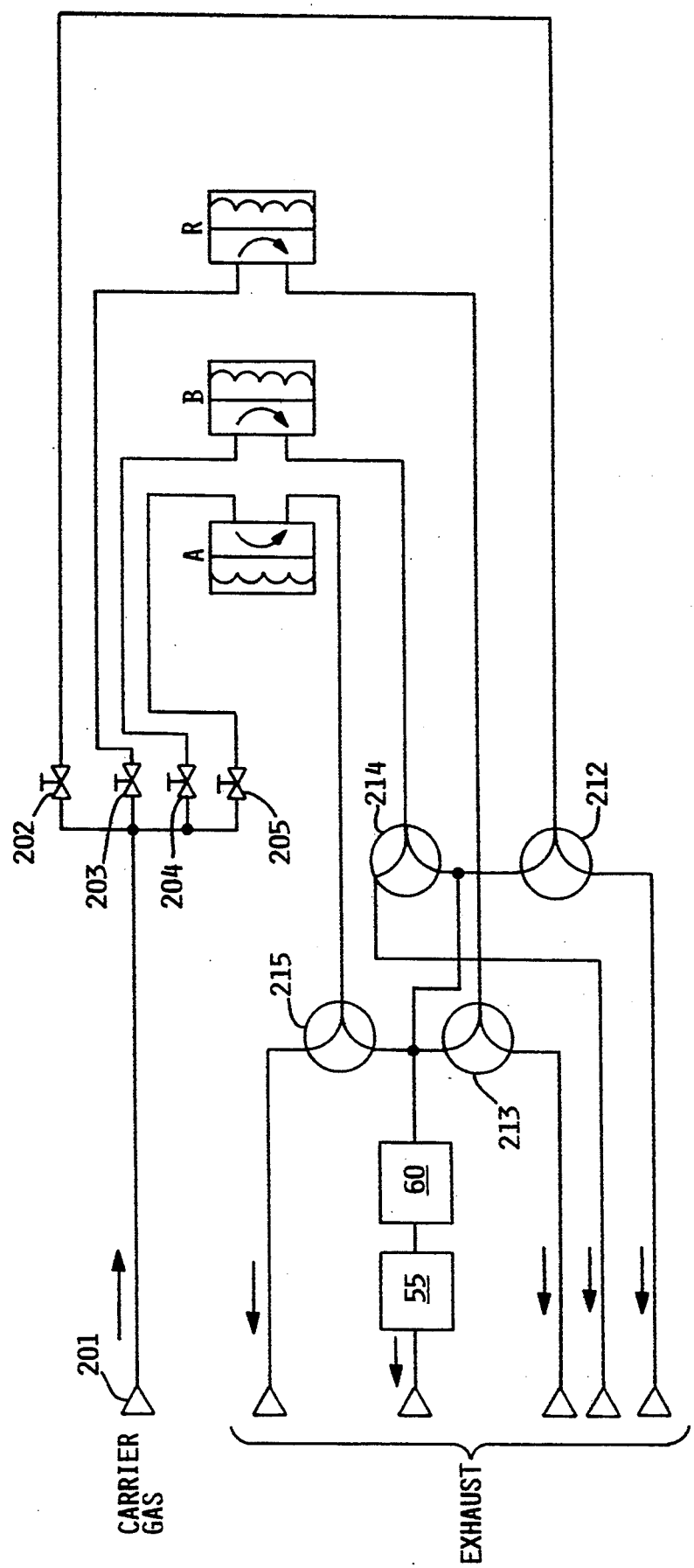
FIG. 2 is a diagrammatic representation of a multiple cell version of the present invention.

FIG. 2 shows a diagrammatic representation of the present invention in conjunction with multiple diffusion cells A, B, . . . R. A suitable carrier gas inlet 201 is coupled to a source of carrier gas, and is conveyed via gas flow conduits to valves 202, 203, 204, and 205. Valves 202-205 are metering valves to regulate the volume flow rate of the carrier gas through the system. Metering valve 202 is connected to a flow control valve 212, which is a three-way valve to convey the gas either to an exhaust outlet or to IR gas analyzer 60. Therefore, the gas flow path comprising metering valve 202 and flow control valve 212 may be considered a purge system, providing a path for pure carrier gas to pass through the system.

Metering valve 203 conveys carrier gas to a diffusion cell R, and from cell R to flow control valve 213. Flow control valve 213 is a three-way valve which either connects to an exhaust port or to IR gas analyzer 60. Metering valve 204 conveys the carrier gas to a diffusion cell B, and therefrom to a flow control valve 214. Flow control valve 214 is a three-way valve which may be set to either convey the gas to an exhaust outlet or to IR gas analyzer 60. Metering valve 205 conveys the carrier gas to diffusion cell A, and from there to flow control valve 215. Flow valve 215 is a three-way valve which may be set to deliver gas either to an exhaust outlet or to IR gas analyzer 60. An outlet from IR gas analyzer 60 is conveyed to flow meter 55, and from flow meter 55 the gas is conveyed to an exhaust outlet. In each case, the respective cells A, B, . . . R, have one of their chambers filled or partially filled with water and the other chamber coupled to a carrier gas flow path. By selectively adjusting the metering valves 202-205, and also adjusting the flow control valves 212-215, one may purge the system or monitor and select the respective water vapor measurements for these selected cells, and each cell may be set up to test a different material for permeability.

Figure 3:
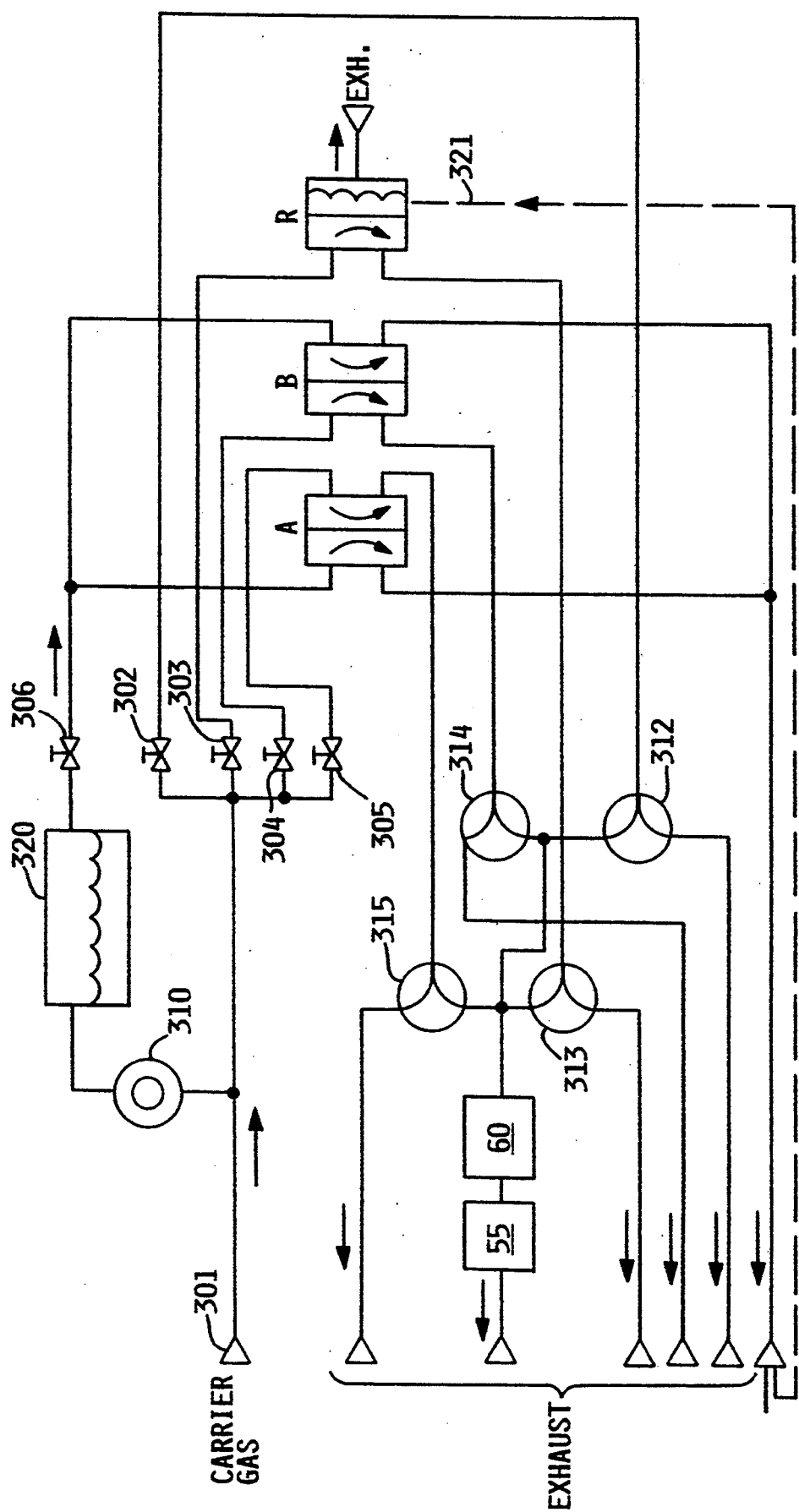
FIG. 3 is a diagrammatic representation of a multiple cell version of the invention utilizing controlled relative humidity to produce the water vapor.

FIG. 3 shows a diagrammatic representation of an alternate embodiment of the present invention, wherein the amount of water vapor introduced into one or more cells may be controlled, by controlling the relative humidity of a gas flow into one or more of the cell chambers. A carrier gas inlet 301 is coupled to metering valves 302-305 for purging or for regulating the volume flow rate of carrier gas into the various diffusion cells. Additionally, the carrier gas is coupled to a relative humidity generator 320 via an on/off valve 310. Relative humidity generator 320 is coupled to a metering valve 306 and from there to one or more test cells A, B. The relative humidity generator 320 and a suitable system for utilizing the relative humidity generator is disclosed in U.S. Pat. No. 5,107,696, issued Apr. 28, 1992, which is incorporated by reference herein. Typically, relative humidity may be controlled reasonably within the range of 0-90 percent, and the humid gas therefrom may be coupled into one of the chambers of each of the test cells A, B. Further, the humid gas conveyed through cells A, B, may be also coupled to cell R, as is shown by dotted line 321. Alternatively, diffusion cell R may be super saturated by partially filling one of the cell chambers with water, as has been described herein. The unhumidified carrier gas passes through metering valves 302-305 into respective second chambers of the diffusion cells A, B, . . . R, and from there to respective flow control valves 312-315. Each of the flow control valves 312-315 may be selectively positioned to pass the carrier gas into the IR gas analyzer 60, and from there into the flow meter 55. The advantage of the embodiment shown in FIG. 3 is that it enables the permeability measurement of membranes under variable relative humidity conditions, and wherein the relative humidity is known and adjustable.

In operation, samples of the selected packaging and/or film materials are respectively clamped into the various diffusion cells for testing. The diffusion cells are then either filled or partially filled with water, or coupled to the suitable relative humidity generator, and the metering valves for passing carrier gas into the respective diffusion cells are selectively positioned. When the desired carrier gas flow rate has been established, the carrier gas passes through the diffusion cells and into the IR gas analyzer 60. A certain amount of water vapor diffuses through the film material undergoing tests and is picked up by the carrier gas passing through the diffusion cell. The water vapor and carrier gas mixture is conveyed to IR gas analyzer 60 where it is diffused throughout the absorption cell by the pulsating action of bellows 76. Bellows 76 is driven by a mechanical linkage 78, coupled to a rotating drive source 80. The cyclical compression of the bellows 76 will correspondingly compress the carrier gas and water vapor present in the absorption cell, making it less transparent to IR energy, and when the bellows 76 expands the water vapor content of the absorption cell correspondingly expands, making the cell more transparent to IR energy. This results in a fluctuating AC signal being developed at photocell 66, the magnitude of which is representative of the relative water vapor content within absorption cell 52. If no water vapor exists within absorption cell 52 the radiant energy passing through cell 52 will not be modulated and photocell 66 will generate a direct current signal. The signal from photocell 66 is amplified in amplifier 68, and is adjusted inversely according to the flow rate through flow meter 55, by adjustment of the gain of amplifier 69. The adjusted signal is coupled to a strip chart recorder 72 or other suitable display device, wherein a time plot of the water vapor content is presented, as illustrated by curve 72a on strip chart recorder 72. If multiple diffusion cells are used, each diffusion cell may be connected into the IR gas analyzer and flow meter system in sequence, so as to record the multiple permeability measurements for a plurality of films. In some cases, it may be advisable to designate one of the cells as a "reference" cell, wherein a known film permeability is utilized in conjunction with a known water vapor or relative humidity content. The measurements taken from the reference cell can then be utilized as a base line comparison to the measurements from the remaining cells, so as to form a basis for comparing or checking the overall results.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A system for measuring the permeability of a membrane to water vapor, comprising:
   a) a diffusion cell having said membrane clamped between a first and second chamber, including means for introducing water vapor into said first chamber and means for introducing a flow of carrier gas through said second chamber;
   b) an infrared gas analyzer connected in gas flow relation to said second chamber, said analyzer having means for generating an electrical signal representative of the water vapor content of said carrier gas;
   c) a gas flow sensor connected in gas flow relation to said second chamber, said sensor having means for generating an electrical signal representative of the flow rate of said carrier gas;
   d) a variable gain amplifier connected to receive said water vapor-representative signal and to receive said flow rate-representative signal, whereby said flow rate-representative signal varies the amplification gain of said amplifier; and
   e) means for displaying the output signal from said variable gain amplifier.

2. The apparatus of claim 1, wherein said means for displaying further comprises a strip chart recorder.

3. The apparatus of claim 1, wherein said means for introducing water vapor further comprises a relative humidity generator.

4. The apparatus of claim 1, wherein said infrared gas analyzer further comprises an absorption cell having infrared transmitting windows therein, a source of infrared radiation position to radiate energy through said windows, an optical filter positioned to pass selected wavelengths of said radiation and a photocell positioned to receive radiation passing said optical filter.

5. The apparatus of claim 4, wherein said infrared gas analyzer further comprises a reciprocable air pumping system coupled into said absorption cell.

6. The apparatus of claim 5, wherein said optical filter further comprises a bandpass filter at 2.6 microns.

7. Apparatus for measuring water vapor permeability of a material, comprising:
   a) a plurality of diffusion cells, each cell having means for clamping said material between a first and second chamber;
   b) means for introducing a source of water vapor into each first chamber of said plurality of cells;
   c) means for connecting a source of carrier gas to each second chamber of said plurality of cells, and a gas outlet port in each second chamber of said plurality of cells;
   d) a plurality of valves, each of said valves having an inlet connected to a gas outlet port of one of said second chambers, and each of said valves having a first exhaust outlet and a second outlet;
   e) a gas analyzer device connected to all of said second outlets, said gas analyzer device having means for measuring the water vapor content of said carrier gas, and generating a first electrical signal representative thereof;
   f) a gas flow measuring device connected to said gas analyzer device, said gas flow measuring device having means for measuring the volume flow rate of said carrier gas, and generating a second electrical signal representative thereof;
   g) a variable gain amplifier connected to receive said first and second electrical signals, whereby the gain of said amplifier is controlled by said second electrical signal; and
   h) a display device connected to said variable gain amplifier.

* * * * *